(12) United States Patent
Fiss et al.

(10) Patent No.: US 7,989,168 B2
(45) Date of Patent: Aug. 2, 2011

(54) PROOFREADING PRIMER EXTENSION

(75) Inventors: Ellen Fiss, Albany, CA (US); Thomas William Myers, Dublin, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 12/538,971

(22) Filed: Aug. 11, 2009

(65) Prior Publication Data

US 2010/0041053 A1  Feb. 18, 2010

Related U.S. Application Data

(60) Provisional application No. 61/188,841, filed on Aug. 12, 2008.

(51) Int. Cl.
*C12Q 1/68* (2006.01)

(52) U.S. Cl. ........................................ 435/6.1

(58) Field of Classification Search .................. None
See application file for complete search history.

(56) References Cited

U.S. PATENT DOCUMENTS

| | | | |
|---|---|---|---|
| 2002/0150900 A1 | 10/2002 | Marshall et al. | |
| 2005/0037991 A1 | 2/2005 | Bodepudi et al. | |
| 2006/0088855 A1* | 4/2006 | Chou et al. | 435/6 |
| 2006/0105348 A1* | 5/2006 | Lee et al. | 435/6 |
| 2007/0219361 A1 | 9/2007 | Bodepudi et al. | |

FOREIGN PATENT DOCUMENTS

| | | |
|---|---|---|
| EP | 1167524 A1 | 1/2002 |
| EP | 1167524 B1 | 5/2007 |
| EP | 2009005770 | 8/2009 |
| WO | 2005012499 A2 | 2/2005 |
| WO | 2005012499 A3 | 2/2005 |

OTHER PUBLICATIONS

Fujiwara et al. (PCR Methods Appl. Feb. 1995;4(4):239-40).*
Bi, Wanli et al.; "Detection of known mutation by proor-reading PCR"; 1998, *Nucleic Acids Research*, vol. 26, No. 12, pp. 3073-3075.
Brautigam, Chad A. et al.; "Structural Principles for the Inhibition of the 3'-5' Exonuclease Activity of *Escherichia coli* DNA Polymerase I by Phosphorothioates"; 1998, *J. Mol. Bio.*, vol. 277, pp. 363-377.
Di Giusto, Daniel A. et al.; "Strong positional preference in the interaction of LNA oligonucleotides with DNA polymerase and proofreading exonuclease activities: implications for genotyping assays"; 2004, *Nucleic Acids Research*, vol. 32, No. 3, pp. 1-8.
Gale, James M.; "Evaluation of 15 Polymerases and Phosphorothioate Primer Modification for Detection of UV-induced C:G to T:A Mutations by Allele-specific PCR"; 2004, *Photochemistry and Photobiology*, 12 pages.
Limones, G.R. et al.; "A novel quantitative real-time PCR test for *Mycobacterium tuberculosis*"; 2006 *CLI*, 2 pages.
Lin-Ling, Chen et al.; "Single-base Discrimination Mediated by Profreading Inert Allele Specific Primers"; 2005, *Journal of Biochemistry and Molecular Biology*, vol. 38, No. 1, pp. 24-27.
Schonbrunner, Nancy J. et al.; "Chimeric Thermostable DNA Polymerases with Reverse Transcriptase and Attenuated 3'-5' Exonuclease Activity"; 2006, *Biochemistry*, vol. 45, pp. 12786-12795.
Skerra, Arne; "Phosphorothioate primers improve the amplification of DNA sequences by DNA polymerases with proofreading activity"; 1992, *Nucleic Acids Research*, vol. 20, No. 14, pp. 3551-3554.
Yang, Hui-Ling et al.; "High fidelity PCR with an off/on switch mediated by proofreading polymerases combining with phosphorothioate-modified primer"; 2005, *Biochemical and Biophysical Research Communication*, vol. 328, pp. 265-272.
Zhang, Jia et al.; "Proofreading genotyping assays mediated by high fidelity exo+ DNA polymerases"; 2005, *Trends in Biotechnology*, vol. 23, No. 2, pp. 92-96.
Fujiwara, Hiroshi, et al, 1994, "PCR with Deoxyinosine-containing Primers Using DNA Polymerases with Proofreading Activitiy", PCR Methods and Applications, 239-240.

* cited by examiner

*Primary Examiner* — Christopher M. Babic
(74) *Attorney, Agent, or Firm* — Rhea Cyd Nersesiai

(57) ABSTRACT

The present invention provides for primer extension reactions, including polymerase chain reactions, in which a polymerase having 3'-5' exonuclease activity edits a primer that is not fully complementary thereby allowing for amplification and detection of target nucleic acids that may have variability in their sequences.

9 Claims, 7 Drawing Sheets

FIG. 2A

Primers and Templates in HIV GAG Region

| | Upstream Primer | | RT Primers |
|---|---|---|---|
| | AGTGGGGGACATCAAGCAGCCATGEAAAA | (-1) | GGTACTAGTAGTTCCTGCTATGTCACTTEC |
| | | (-6) | GGTACTAGTAGTTCCTGCTATGTCACTTCC |
| | | (-6) | GGTACTAGTAGTTCCTGCTATGTEACTTPQ |
| Transcripts | | | |
| Matched | ·················· | ·· | ····················· |
| Mismatched | ···A······G····· | ·· | ················CC·· |

Key: Mismatches are in bold/underlined; E = 2'-amino (ribo) C; P = ethyl-dC; Q = t-butyl benzyl-dC

PROOFREADING PRIMER EXTENSION

CROSS-REFERENCE TO RELATED PATENT APPLICATIONS

The present application claims benefit of priority to U.S. Provisional Patent Application No. 61/188,841, filed Aug. 12, 2008, which is incorporated by reference for all purposes.

BACKGROUND OF THE INVENTION

The development of nucleic acid amplification technology has revolutionized genetic analysis and engineering science. For example, the polymerase chain reaction (PCR) is commonly utilized to amplify specific target nucleic acids using selected primer nucleic acids, e.g., to facilitate the detection of the target nucleic acid as part of a diagnostic, forensic, or other application. Primers typically function in pairs that are designed for extension towards each other to cover the selected target region. A typical PCR cycle includes a high temperature (e.g., 85° C. or more) denaturation step during which the strands of double-stranded nucleic acids separate from one another, a low temperature (e.g., 45-65° C.) annealing step during which the primers hybridize to the separated single strands, and an intermediate temperature (e.g., around 72° C.) extension step during which a nucleic acid polymerase extends the primers. Two-temperature thermocycling procedures are also utilized. These generally include a high temperature denaturation step and a low temperature anneal-extend step.

PCRs are also described in many different U.S. patents including, e.g., U.S. Pat. No. 4,683,195, entitled "PROCESS FOR AMPLIFYING, DETECTING, AND/OR-CLONING NUCLEIC ACID SEQUENCES," which issued to Mullis et al. Jul. 28, 1987, U.S. Pat. No. 4,683,202, entitled "PROCESS FOR AMPLIFYING NUCLEIC ACID SEQUENCES," which issued to Mullis Jul. 28, 1987, and U.S. Pat. No. 4,965,188, entitled "PROCESS FOR AMPLIFYING, DETECTING, AND/OR CLONING NUCLEIC ACID SEQUENCES USING A THERMOSTABLE ENZYME," which issued to Mullis et al. Oct. 23, 1990, which are each incorporated by reference. Further, PCR-related techniques are also described in various other publications, such as Innis et al. (Eds.) *PCR Protocols: A Guide to Methods and Applications*, Elsevier Science & Technology Books (1990), Innis et al. (Eds.) *PCR Applications: Protocols for Functional Genomics*, Academic Press (1999), Edwards et al., *Real-Time PCR*, Taylor & Francis, Inc. (2004), and Rapley et al., *Molecular Analysis and Genome Discovery*, John Wiley & Sons, Inc. (2004).

BRIEF SUMMARY OF THE INVENTION

The present invention provides methods of performing a primer extension reaction. In some embodiments, the methods comprise:
a. contacting an oligonucleotide to (i) a template nucleic acid and (ii) a nucleic acid polymerase having 3'-5' exonuclease activity, wherein:
   i. the oligonucleotide comprises a modified nucleotide that is not removed by the 3'-5' exonuclease activity;
   ii. the modified nucleotide is not at the 3' or 5' terminal nucleotide nor at the 3' penultimate nucleotide of the oligonucleotide;
   iii. the oligonucleotide has a 3' portion and a 5' portion, wherein the 3' portion comprises the nucleotides in the oligonucleotide that are 3' of the modified nucleotide and the 5' portion comprises the nucleotides in the oligonucleotide that are 5' of the modified nucleotide; and
   iv. the contacting step is performed under conditions suitable to allow the polymerase to edit the 3' portion of the oligonucleotide in a template-specific manner if the 3' portion of the oligonucleotide is not 100% complementary to the template nucleic acid; and
b. performing a primer extension reaction by extending the oligonucleotide in a template-dependent manner.

In some embodiments, the 3' portion of the oligonucleotide, before editing, is between 70-100% complementary to the template nucleic acid.

In some embodiments, the template nucleic acid is from a biological sample. In some embodiments, the template nucleic acid is from a viral or bacterial genome.

In some embodiments, the template nucleic acid is RNA. In some embodiments, the template nucleic acid is DNA.

In some embodiments, the modified nucleotide is comprises moiety other than —H at the 2' position. In some embodiments, the modified nucleotide comprises a 2' moiety selected from the group consisting of amino, O-methyl, OH, O-phosphate, and phosphorothioate.

In some embodiments, the modified nucleotide is between 2-10 nucleotides from the 3' end of the oligonucleotide. In some embodiments, the modified nucleotide is between 5-7 nucleotides from the 3' end of the oligonucleotide.

In some embodiments, the oligonucleotide is:
between 15-40 nucleotides long;
is at least 70% complementary to the template nucleic acid across the entire length of the oligonucleotide; and/or
the modified nucleotide is between 2-10 nucleotides from the 3' end of the oligonucleotide.

In some embodiments, the polymerase comprises a thermally reversible covalent modification, wherein incubation at a temperature greater than 50° C. in an aqueous buffer at alkaline pH reverse the covalent modification and results in at least two-fold increase in enzyme activity in less than 20 minutes.

In some embodiments, step b comprises a polymerase chain reaction. In some embodiments, step b comprises performing a real-time polymerase chain reaction.

In some embodiments, the modified nucleotide does not comprise a fluorescent moiety.

The present invention also provides reaction mixtures comprising one or more of the reagents described herein. In some embodiments, the reaction mixtures comprise an oligonucleotide, the oligonucleotide comprising a modified nucleotide that is not removed by 3'-5' exonuclease activity of a nucleic acid polymerase, wherein the modified nucleotide is not at the 3' or 5' terminal nucleotide nor at the 3' penultimate nucleotide of the oligonucleotide and the modified nucleotide does not comprise a fluorescent moiety.

In some embodiments, the reaction mixture further comprises a nucleic acid polymerase having 3'-5' exonuclease activity. In some embodiments, the reaction mixture further comprises a template nucleic acid. In some embodiments, the reaction mixture further comprises deoxynucleoside triphosphates.

In some embodiments, the oligonucleotide is between 15-40 nucleotides long.

In some embodiments, the modified nucleotide is between 3-10 nucleotides from the 3' end of the oligonucleotide.

In some embodiments, the modified nucleotide comprises a moiety other than —H at the 2' position. In some embodiments, the modified nucleotide comprises a 2' moiety selected from the group consisting of amino, O-methyl, OH, O-phosphate, and phosphorothioate.

The present invention further includes kits comprising one or more reagents as described herein. In some embodiments, the kit comprises an oligonucleotide, the oligonucleotide comprising a modified nucleotide that is not removed by 3'-5' exonuclease activity of a nucleic acid polymerase, wherein the modified nucleotide is not at the 3' or 5' terminal nucleotide nor at the 3' penultimate nucleotide of the oligonucleotide and the modified nucleotide does not comprise a fluorescent moiety.

In some embodiments, the kit further comprises a nucleic acid polymerase having 3'-5' exonuclease activity.

In some embodiments, the kit further comprises deoxynucleoside triphosphates.

In some embodiments, the oligonucleotide is between 15-40 nucleotides long.

In some embodiments, the modified nucleotide is between 3-10 nucleotides from the 3' end of the oligonucleotide. In some embodiments, the modified nucleotide comprises a moiety other than —H or —OH at the 2' position. In some embodiments, the modified nucleotide comprises a 2' moiety selected from the group consisting of amino, O-methyl, —OH, O-phosphate, and phosphorothioate.

The present invention also provides an oligonucleotide comprising a modified nucleotide that is not removed by 3'-5' exonuclease activity of a nucleic acid polymerase, wherein the modified nucleotide is not at the 3' or 5' terminal nucleotide nor at the 3' penultimate nucleotide of the oligonucleotide and the modified nucleotide does not comprise a fluorescent moiety.

In some embodiments, the oligonucleotide is between 15-40 nucleotides long.

In some embodiments, the modified nucleotide is between 3-10 nucleotides from the 3' end of the oligonucleotide.

In some embodiments, the modified nucleotide comprises a moiety other than —H or —OH at the 2' position. In some embodiments, the modified nucleotide comprises a 2' moiety selected from the group consisting of amino, O-methyl, OH, O-phosphate, and phosphorothioate.

The present invention also provides methods of detecting the presence, absence or amount of a biological entity in a biological sample. In some embodiments, the method comprises, a. contacting an oligonucleotide to (i) a biological sample suspected of having a nucleic acid from the biological entity and (ii) a nucleic acid polymerase having 3'-5' exonuclease activity, wherein the oligonucleotide is substantially complementary to the nucleic acid from the biological entity;

b. performing a polymerase chain reaction thereby extending the oligonucleotide in a template-dependent manner to produce a polynucleotide product complementary to the nucleic acid from the biological entity;

c. quantifying the polynucleotide product, or its complement; and d. correlating the amount of polynucleotide product, or complement thereof, to the amount or presence or absence of the biological entity in the biological sample.

In some embodiments, the quantifying step comprises quantitative real-time PCR.

In some embodiments, the biological entity is a virus, bacteria or cancer cell. In some embodiments, the virus is an HIV, HBV, or HCV.

In some embodiments, the PCR comprises a step under conditions that allow extension of the oligonucleotide whether or not there are zero, one, two or three mismatches between the oligonucleotide and the viral nucleic acid. In some embodiments, the oligonucleotide has one or more mismatch with the nucleic acid from the biological entity and wherein the 3'-5' exonuclease activity of the polymerase edits the oligonucleotide to result in a polynucleotide product that is fully complementary to the polynucleotide product.

In some embodiments, the performing step further comprises one or more polymerase, some of which substantially lack 3'-5' exonuclease activity.

In some embodiments, the performing step does not include a polymerase lacking or substantially lacking 3'-5' exonuclease activity.

Definitions

The terms "a," "an," and "the" include plural referents, unless the context clearly indicates otherwise.

The term "nucleic acid" refers to a polymer of monomers that can be corresponded to a ribose nucleic acid (RNA) or deoxyribose nucleic acid (DNA) polymer, or analog thereof. This includes polymers of nucleotides such as RNA and DNA, as well as modified forms thereof, peptide nucleic acids (PNAs), locked nucleic acids (LNA™), and the like. In certain applications, the nucleic acid can be a polymer that includes multiple monomer types, e.g., both RNA and DNA subunits. A nucleic acid can be or include, e.g., a chromosome or chromosomal segment, a vector (e.g., an expression vector), an expression cassette, a naked DNA or RNA polymer, an amplicon, an oligonucleotide, a primer, a probe, etc. A nucleic acid can be e.g., single-stranded or double-stranded. Unless otherwise indicated, a particular nucleic acid sequence optionally comprises or encodes complementary sequences, in addition to any sequence explicitly indicated.

A nucleic acid is typically single-stranded or double-stranded and will generally contain phosphodiester bonds, although in some cases, as outlined herein, nucleic acid analogs are included that may have alternate backbones, including, for example and without limitation, phosphoramide (Beaucage et al. (1993) *Tetrahedron* 49(10):1925 and the references therein; Letsinger (1970) *J. Org. Chem.* 35:3800; Sprinzl et al. (1977) *Eur. J. Biochem.* 81:579; Letsinger et al. (1986) *Nucl. Acids Res.* 14: 3487; Sawai et al. (1984) *Chem. Lett.* 805; Letsinger et al. (1988) *J. Am. Chem. Soc.* 110:4470; and Pauwels et al. (1986) *Chemica Scripta* 26:1419), phosphorothioate (Mag et al. (1991) *Nucleic Acids Res.* 19:1437 and U.S. Pat. No. 5,644,048), phosphorodithioate (Briu et al. (1989) *J. Am. Chem. Soc.* 111:2321), O-methylphosphoroamidite linkages (Eckstein, *Oligonucleotides and Analogues: A Practical Approach*, Oxford University Press (1992)), and peptide nucleic acid backbones and linkages (Egholm (1992) *J. Am. Chem. Soc.* 114:1895; Meier et al. (1992) *Chem. Int. Ed. Engl.* 31:1008; Nielsen (1993) *Nature* 365:566; and Carlsson et al. (1996) *Nature* 380:207), which references are each incorporated by reference. Other analog nucleic acids include those with positively charged backbones (Denpcy et al. (1995) *Proc. Natl. Acad. Sci. USA* 92:6097); non-ionic backbones (U.S. Pat. Nos. 5,386,023, 5,637,684, 5,602,240, 5,216,141 and 4,469,863; Angew (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghvi and P. Dan Cook; Mesmaeker et al. (1994) *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (Jenkins et al. (1995) *Chem. Soc. Rev.* pp 169-176, which is incorporated by reference). Several nucleic acid analogs are also described in, e.g., Rawls, *C & E News* Jun. 2, 1997 page 35, which is incorporated by reference. These modifications of the ribose-phosphate backbone may be done to facilitate the addition of additional moieties such as labeling moieties, or to alter the stability and half-life of such molecules in physiological environments.

In addition to naturally occurring heterocyclic bases that are typically found in nucleic acids (e.g., adenine, guanine, thymine, cytosine, and uracil), nucleic acid analogs also include those having non-naturally occurring heterocyclic or other modified nucleotides, many of which are described, or otherwise referred to, herein. In particular, many non-naturally occurring bases are described further in, e.g., Seela et al. (1991) *Helv. Chim. Acta* 74:1790, Grein et al. (1994) *Bioorg. Med. Chem. Lett.* 4:971-976, and Seela et al. (1999) *Helv. Chim. Acta* 82:1640, which are each incorporated by reference. To further illustrate, certain bases used in nucleotides that act as melting temperature (Tm) modifiers are optionally included. For example, some of these include 7-deazapurines (e.g., 7-deazaguanine, 7-deazaadenine, etc.), pyrazolo[3,4-d] pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

Additional examples of modified nucleotides and nucleotides are also described in, e.g., U.S. Pat. No. 5,484,908, entitled "OLIGONUCLEOTIDES CONTAINING 5-PROPYNYL PYRIMIDINES," issued Jan. 16, 1996 to Froehler et al., U.S. Pat. No. 5,645,985, entitled "ENHANCED TRIPLE-HELIX AND DOUBLE-HELIX FORMATION WITH OLIGOMERS CONTAINING MODIFIED PYRIMIDINES," issued Jul. 8, 1997 to Froehler et al., U.S. Pat. No. 5,830,653, entitled "METHODS OF USING OLIGOMERS CONTAINING MODIFIED PYRIMIDINES," issued Nov. 3, 1998 to Froehler et al., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference.

An "oligonucleotide" refers to a nucleic acid that includes at least 6 nucleic acid monomer units (e.g., nucleotides), e.g., at least 8, 10, 12, or 15 monomer units. The exact size of an oligonucleotide generally depends on various factors, including the ultimate function or use of the oligonucleotide. Typically, the nucleotide monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) *Meth. Enzymol.* 68:90-99; the phosphodiester method of Brown et al. (1979) *Meth. Enzymol.* 68:109-151; the diethylphosphoramidite method of Beaucage et al. (1981) *Tetrahedron Lett.* 22:1859-1862; the triester method of Matteucci et al. (1981) *J. Am. Chem. Soc.* 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art.

The term "thermostable polymerase," refers to an enzyme that is stable to heat (e.g., 90-95° C.), is heat resistant, and retains sufficient activity to effect subsequent primer extension reactions and does not become irreversibly denatured (inactivated) when subjected to the elevated temperatures for the time necessary to effect denaturation of double-stranded nucleic acids. The heating conditions necessary for nucleic acid denaturation are well known in the art and are exemplified in, e.g., U.S. Pat. Nos. 4,683,202, 4,683,195, and 4,965,188, which are incorporated herein by reference. As used herein, a thermostable polymerase is suitable for use in a temperature cycling reaction such as the polymerase chain reaction ("PCR"). Irreversible denaturation for purposes herein refers to permanent and complete loss of enzymatic activity. For a thermostable polymerase, enzymatic activity refers to the catalysis of the combination of the nucleotides in the proper manner to form primer extension products that are complementary to a template nucleic acid strand. Thermostable DNA polymerases from thermophilic bacteria include, e.g., DNA polymerases from *Thermotoga maritima*, *Thermus aquaticus*, *Thermus thermophilus*, *Thermus flavus*, *Thermus filiformis*, *Thermus* species sps17, *Thermus* species Z05, *Thermus caldophilus*, *Bacillus caldotenax*, *Thermotoga neopolitana*, and *Thermosipho africanus*.

"3'-5' exonuclease activity" as used herein refers to an activity of some polymerases that removes the '3 most base of a nucleic acid. This activity is sometimes referred to in the art as the "proofreading" activity of a polymerase. A polymerase having 3'-5' exonuclease activity is capable of removing one or more 3' nucleotides of an oligonucleotide, i.e., in a sequential manner. The nucleotides can be subsequently replaced with nucleotides in a template-dependent manner, thereby "editing" the nucleotides of the oligonucleotide, i.e., replacing nucleotides that are not complementary to a template nucleic acid with nucleotides that are complementary to the template.

"Substantially lacking 3'-5' exonuclease activity" refers to a 3'-5' exonuclease activity that is less than or equal to 3% (e.g., less than 1% or 0.1%) of the activity in a native *Thermatoga maritima* DNA polymerase. Exemplary polymerases substantially lacking 3'-5' exonuclease activity include those described in, e.g., U.S. Pat. No. 7,148,049.

A "modified nucleotide" as used herein refers to a nucleotide that does not occur naturally in genomic DNA (e.g., a synthetic nucleotide or a ribonucleotide). As described in more detail herein, a base having a substitution at the 2' position of the pentose sugar portion of the nucleotide results in a modified nucleotide that is not removed by 3'-5' activity of DNA polymerases. A "modified nucleotide that is not removed by 3'-5' exonuclease activity of a nucleic acid polymerase" refers to a modified nucleotide which, when at the 3' end, or 3' penultimate position, of an oligonucleotide, is not removed in the presence of a polymerase having 3'-5' exonuclease activity.

A "2' moiety" of a modified nucleotide refers to a moiety linked to the 2' carbon of the sugar portion of the nucleotide, as is commonly used in the nucleic acid arts. See, e.g., US Patent Publication No. 2006/00888555 and 2007/0219361.

A nucleic acid is "complementary" in relation to another nucleic acid when at least a nucleic acid segment (i.e., at least two contiguous bases) can combine in an antiparallel association or hybridize with at least a subsequence of other nucleic acid to form a duplex. The antiparallel association can be intramolecular, e.g., in the form of a hairpin loop within a nucleic acid, or intermolecular, such as when two or more single-stranded nucleic acids hybridize with one another. In the context of the present invention, for an oligonucleotide that is "100% complementary" to a particular sequence (e.g., a template nucleic acid), each base of the oligonucleotide is complementary to the corresponding bases in the particular sequence in an anti-parallel manner. Certain bases not commonly found in natural nucleic acids may be included in the nucleic acids of the present invention and can include, for example, inosine, 7-deazaguanine and those discussed above. In some embodiments, complementarity is not perfect, i.e., nucleic acids can be "substantially complementary" where they have a "percent complementary" indicating that only a certain percentage of nucleotides of an oligonucleotide are complementary to a template, while the remaining nucleotides are not complementary. For example, in some embodiments, the substantially complementary oligonucleotides of the present invention (or their 3' portions) are less than 100% complementary to a template nucleic acid, e.g., at least 60%, 70%, 80%, 85%, 90%, or 95% complementary to the template. For example, in some embodiments, the oligonucleotide (or at least the 3' portion of the oligonucleotide) has 1, 2, 3, 4, 5, 6, or more mismatches with a template nucleic acid. In the typical case where the template nucleic acid is longer than the oligonucleotide (or where indicated, the portion thereof), the percentage or number of mismatches (or complementary nucleotides) is determined with reference to the subsequence of the template nucleic acid of the same length as the oligonucleotide (or where indicated, the portion thereof) with the highest proportion of nucleotides complementary to the oligonucleotide (or portion thereof where indicated).

A "primer extension reaction" refers to a molecular reaction in which a nucleic acid polymerase adds one or more nucleotide to the 3' terminus of a primer in a template-specific manner. Extension does not only refer to the first nucleotide added to the 3' terminus of a primer, but also includes any further extension of a polynucleotide formed by the extended primer.

A "thermally reversible covalent modification" of an enzyme as used herein refers to a reversible chemical modification of an enzyme such that the enzyme is initially substantially inactive at room temperature, but wherein the chemical (e.g., covalent) modification is released at higher temperature (e.g., greater than 50° C.). An example of a thermally reversible covalent inactivation involves chemical modification of lysine residues, e.g., achieved by reaction with acid anhydrides (see, EP 0 962 526).

As used herein, a "biological sample" refers to any substance containing or presumed to contain nucleic acid (e.g., from a bacteria, virus, tissue biopsy etc.). The sample can be obtained by any means known to those of skill in the art. Such sample can be an amount of tissue or fluid, or a purified fraction thereof, isolated from an individual or individuals, including, but not limited to, for example, skin, plasma, serum, whole blood, spinal fluid, saliva, peritoneal fluid, lymphatic fluid, aqueous or vitreous humor, synovial fluid, urine, tears, blood cells, blood products, semen, seminal fluid, vaginal fluids, pulmonary effusion, serosal fluid, organs, bronchio-alveolar lavage, tumors, paraffin embedded tissues, etc. Samples also can include constituents and components of in vitro cell cultures, including, but not limited to, conditioned medium resulting from the growth of cells in the cell culture medium, recombinant cells, cell components, etc. A nucleic acid can be obtained from a biological sample by procedures well known in the art.

BRIEF DESCRIPTION OF THE DRAWINGS

FIG. 2A provides primers (SEQ ID NOS:1-4) and templates (SEQ ID NOS:5-8) used in the examples.

DETAILED DESCRIPTION OF THE INVENTION

I. Introduction

Figure 1:
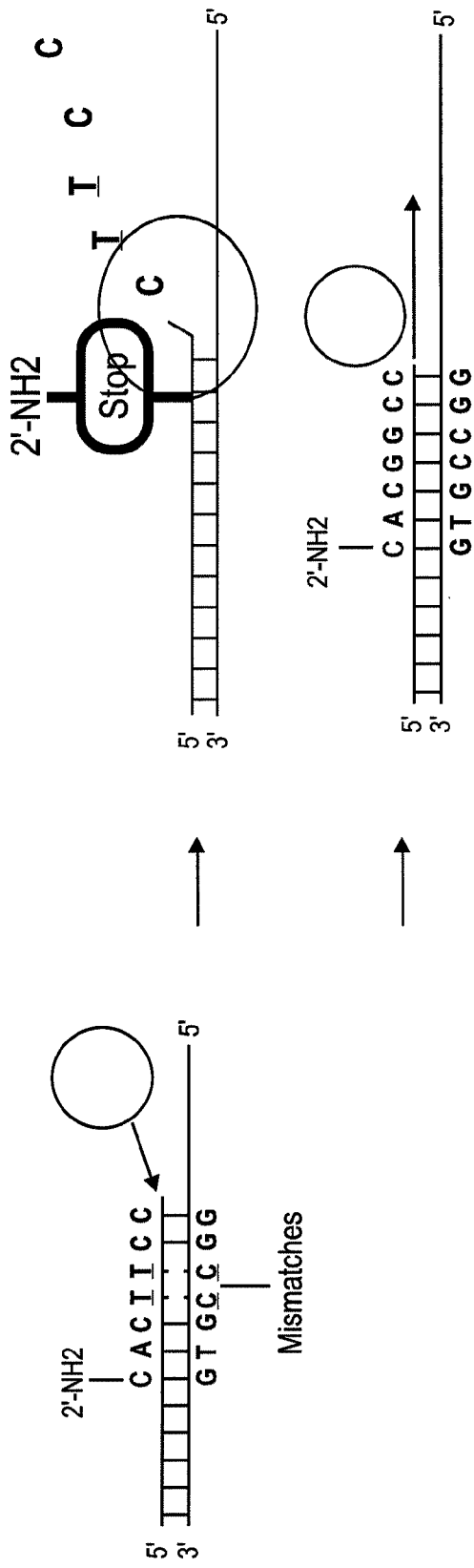
FIG. 1 provides a schematic illustration of mismatch editing. The two Ts in the primer sequence (underlined) are mismatched to the target. The DNA polymerase removes the mismatches on the primer prior to extending it. The primer is protected from further enzymatic degradation by the 2'-amino modification in the primer sequence. This process generates a primer that is perfectly matched to its target.

The present invention allows for the detection of target (i.e., template) nucleic acids in a primer extension reaction where one or more primers in the reaction is or can be less than perfectly complementary for the target nucleic acid to be amplified and detected. This invention is useful, for example, in design of primers for amplification and detection of a variety of targets where a diversity of related sequences could be in a target sequence. As an example, the invention can be used to detect viral pathogens, where the viral pathogens have sufficient variation in their genomes to make it difficult or impossible to design a single or small set of primers that will amplify most or all possible viral genomes.

The present invention provides for quantitative amplification reactions in which a thermostable polymerase having 3'-5' exonuclease activity (sometimes referred to as proofreading activity) is used to amplify a target sequence, e.g., a template that may have some variation such that one or more oligonucleotide primers used in the amplification are not fully complementary with the target. Conditions of the PCR can be set such that the primers retain specificity for the target but nevertheless tolerate some variation (e.g., 1, 2, 3 mismatches) of complementarity between the primer(s) and template. The polymerase under these conditions will edit the oligonucleotide such that the resulting amplification product is fully complementary to the target sequence. Of course, it will be appreciated that the primers may also include one or more nucleotides at the 5' end of the primer that are non-complementary (e.g., for cloning, sequence tagging, labeling, etc.) and that by "fully complementary" it is meant that the resulting reaction products will not include any internal or 3' mismatches that existed between the primer and the template, but still may include 5' non-complementary nucleotides whose function is other than for hybridization with the target.

In some embodiments, the PCR product is more than a simple primer extension reaction (i.e., a reaction wherein the primer is extended by only 1 or 2 nucleotides). For example, in some embodiments, the PCR product is at least 10 nucleotides long, not counting the oligonucleotide sequence itself that is also incorporated into the product.

In some embodiments, the reaction includes more than one polymerase. In some cases, at least one of the polymerases substantially lacks 3'-5' exonuclease activity. In such cases, the ratio of amount of polymerase having 3'-5' exonuclease activity compared to the polymerase substantially lacking such activity can vary. For example, in some embodiments, the amount of the polymerase having the exonuclease activity is less than the amount of polymerase substantially lacking the activity, i.e., in some embodiments, the ratio is less than 1:2, 1:3, 1:4, or 1:10 (having activity/substantially lacking activity). Alternatively, in some embodiments, the amounts of the polymerases in the reaction are substantially equal and in some embodiments, there is more polymerase with exonuclease activity than substantially lacking the activity.

In some embodiments of the invention, the amount of target nucleic acid in the sample is quantified, e.g., using quantitative amplification. Optionally, the quantification is performed without regard to the presence or absence of mismatching between the oligonucleotide primers and the template as the information desired is the presence and amount of a possibly variable template indicating the presence or absence of a pathogen, microbe, cancer cell, etc., not which sequence is present. Once determined, the presence or amount of the template can be correlated to the presence or amount of a biological entity, i.e., a virus, microbe, cancer cell, etc., from which the template originated.

The present invention also provides for oligonucleotides that act as primers in primer extension reactions. Whereas typically primer extension reactions do not involve the use of a polymerase with 3'-5 exonuclease activity due to the resulting lack of specificity that can occur due to degradation of the primer by the 3'-5' activity, the present invention provides for inclusion of at least one enzyme, e.g., a polymerase, having 3'-5' exonuclease activity. However, to prevent degradation of the primer, in some embodiments, the present invention provides for inclusion of a modified nucleotide in the middle of the primer oligonucleotide. Since the modified nucleotide cannot be removed by the 3'-5' exonuclease activity, only the 3' portion of the primer can be edited by the 3'-5' exonuclease activity. This allows for maintenance of some specificity with the 5' non-degraded portion of the primer and thus allows for hybridization and extension of the primer in spite of initial mismatches that might occur between the 3' portion of the primer and potentially variable template.

II. Modified Nucleotides

The invention provides for the use of any type of modified nucleotide so long as the base prevents substantial degradation of an oligonucleotide in the presence of a polymerase having 3'-5' exonuclease activity when the modified nucleotide is at the 3' end of the oligonucleotide in the presence of a template wherein hybridization of the oligonucleotide to the template results in a mismatch of the modified nucleotide with the template.

In some embodiments, the modified nucleotides have a modified 2' position (i.e., wherein the 2' position is not —H (DNA)). The modified nucleotide can comprise, but is not limited to, the following: 2'amino, 2'O-methyl, 2'OH (ribo), 2'O-phosphate, and 2'phosphorothioate.

III. Oligonucleotides of the Invention

The oligonucleotides of the invention can be of any length convenient for use in primer extension reactions. The oligonucleotides of the invention are at least 8 nucleotides long and optionally comprise a modified nucleotide that is not at the 3' or 5' end of the oligonucleotide. The oligonucleotides of the invention that include a modified nucleotide can be described with reference to a 3' and a 5' portion, where the 3' portion refers to the nucleotides 3' of the modified nucleotide in the oligonucleotide and the 5' portion refers to the nucleotides 5' of the modified nucleotide in the oligonucleotide. Aside from the modified nucleotide, as described herein, the remaining nucleotides in the oligonucleotide can include naturally-occurring or synthetic nucleotides (e.g., nucleotide analogs), or a combination thereof. However, generally, the 3' portion of the nucleotide will not include nucleotides that cannot be removed by 3'-5' exonuclease activity of a polymerase.

The 5' portion of the oligonucleotide can be any sequence. For example, the 5' portion of the oligonucleotide can be designed to hybridize (alone or in combination with some or all of the 3' portion) in a primer extension reaction to a target (template) nucleic acid. In some embodiments, where the target nucleic acid can have some variation (e.g., a viral or bacterial genome) the 5' portion can be designed to hybridize to a region of the target sequence that is at least partly conserved. This can be achieved for example, by designing the 5' portion to have a significant number of complementary nucleotides to the target, e.g., at least 80%, 85%, 90%, 95% or 100% complementary to the target nucleic acid.

The length (i.e., number of nucleotides) of the 5' portion of the oligonucleotide can be any length convenient for primer extension. In some embodiments, the 5' portion is at least 3, 4, 5, 6, 7, 8, 9, 10, 11, 12, 13, 14, 15, 20, 25, 30, 35, 40, or more nucleotides. For example, in some embodiments, the 5' portion is between 6-50 nucleotides, e.g., 10-20, 8-20, 15-50, 20-50, 25-50, 15-40, 20-40 nucleotides long.

The 3' portion of the oligonucleotide can also be of any length useful for the primer extension reaction. As the 3' portion can be edited by the 3'-5' exonuclease activity of the polymerase, in some embodiments, the 3' portion will play less of a role in controlling specificity of the primer extension reaction than the 5' portion. Thus, in some embodiments, the length of the 3' portion will be shorter than the 5' portion. Thus, for example, in some embodiments, the 3' portion is between 1-15 nucleotides, e.g., 1-10, 1-5, 1-4, 1-3, 1-2, 2-10, 2-8, 2-5, 3-10, 3-8 nucleotides long. In some embodiments, the 3' portion is 1, 2, 3, 4, 5, 6, 7, 8, 9, 10 or more nucleotides long.

Optionally, the oligonucleotides of the invention can be labeled or have other moieties covalently or otherwise linked. In some embodiments, the oligonucleotides of the invention do not include a label. In some embodiments, the oligonucleotides of the invention do not include a fluorescent label. In embodiments in which the oligonucleotides of the invention are labeled, any label can be used. An oligonucleotide can be labeled, if desired, by incorporating a label detectable by, e.g., spectroscopic, photochemical, biochemical, immunochemical, chemical, or other techniques. To illustrate, useful labels include radioisotopes, fluorescent dyes, electron-dense reagents, enzymes (as commonly used in ELISAs), biotin, or haptens and proteins for which antisera or monoclonal antibodies are available. Many of these and other labels are described further herein and/or otherwise known in the art.

In certain embodiments of the invention, the label is a fluorescent dye or fluorophore. Typically, a particular fluorophore can emit light of a particular wavelength following absorbance of light of shorter wavelength. The wavelength of the light emitted by a particular fluorophore is characteristic of that fluorophore. Thus, a particular fluorophore can be detected by detecting light of an appropriate wavelength following excitation of the fluorophore with light of shorter wavelength. Fluorescent labels may include dyes that are negatively charged, such as dyes of the fluorescein family, or dyes that are neutral in charge, such as dyes of the carboxyrhodamine family, or dyes that are positively charged, such as dyes of the cyanine family or the rhodamine family. Other families of dyes that can be used in the invention include, e.g., polyhalofluorescein-family dyes, hexachlorofluorescein-family dyes, coumarin-family dyes, oxazine-family dyes, thiazine-family dyes, squaraine-family dyes, chelated lanthanide-family dyes, ALEXA FLUOR® dyes, and BODIPY®-family dyes. Dyes of the fluorescein family include, e.g., FAM, HEX, TET, JOE, NAN and ZOE. Dyes of the carboxyrhodamine family include Texas Red, ROX, R110, R6G, and TAMRA. FAM, HEX, TET, JOE, NAN, ZOE, ROX, R110, R6G, and TAMRA are marketed by Perkin-Elmer (Foster City, Calif.), while Texas Red is marketed by Molecular Probes, Inc. (Eugene, Oreg.). Dyes of the cyanine family include Cy2, Cy3, Cy3.5, Cy5, Cy5.5, and Cy7 and are marketed by Amersham GE Healthcare (Piscataway, N.J.).

IV. Polymerases with 3'-5' Exonuclease Activity

Any polymerase having 3'-5' exonuclease activity can be used as described herein. Representative polymerases having 3'-5' exonuclease activity (including thermostable polymerases) include, e.g., DNA polymerases from *Thermotoga maritima* (Tma [including but not limited to Tma D323A E325A], UlTma, Tma25, etc. [see, e.g., U.S. Pat. No. 6,228, 628]), Tma/Z05 chimeras (see, e.g., Schonbrunner et al., *Biochemistry* 45:12786-12795 (2006)), *Pyrodictium* species, including but not limited to: *Pyrodictium occultum* (Poc) [forms 1 and 2] and *Pyrodictium abyssi* (Pab) [forms 1 and 2], and *Thermosipho africanus* (Taf). Other DNA polymerases containing 3'-5' exonuclease activity include, for example, *Escherichia coli* (*E. coli*-DNA pol I, Klenow Fragment); phi29 DNA polymerase; T4 DNA polymerase; T7 DNA polymerase; *Thermococcus litoralis* (Tli, a.k.a. Vent & Deep Vent); *Pyrococcus furiosus* (Pfa); *Pyrococcus* sp. strain KOD1; *Thermococcus* sp. TY; *Thermococcus* sp. 9°N-7; *Methanococcus jannaschii*; *Bacillus caldotenax* (Bca); *Sulfolobus acidocaldarius* (Sac); *Thermoplasma acidophilum* (Tac); *Methanobacterium thermoautotrophicum* (Mth); *Thermococcus gorgonarius* (RAS Tgo). Additional commercially available polymerases having 3'-5' exonuclease activity include, but are not limited to: those sold by Invitrogen (e.g., AccuPrime™ containing Taq DNA polymerase and a 3'-5' exonuclease containing DNA polymerase derived from *Pyrococcus* species GB-D polymerase; Pfx50™ DNA Polymerase derived from the archaean *Thermococcus zilligii*; AccuPrime™ Pfx DNA Polymerase DNA polymerase derived from *Thermococcus* species strain KOD), Qiagen (e.g., HotStar™ and ProofStart™), and Stratagene (EXL™ DNA polymerase, Taq DNA polymerase and the Archae-Maxx® polymerase enhancing factor). See also, U.S. Pat. No. 5,747,298.

In some embodiments, the polymerases of the invention include modifications of native polymerases such that the polymerases have improved activity. For example, in some embodiments, the polymerases are modified such that that fluorescently labeled nucleotides are incorporated with reduced discrimination relative to non-labeled nucleotides compared to the most closely related native polymerase. For example, modification of the amino acid at "position 4" as described in US Patent Publication No. 2003/0152988 can be used to reduce discrimination. Other useful mutations are described in, e.g., U.S. Pat. No. 7,148,049.

V. Reversible Chemical Modifications

In some embodiments, the polymerases used in the invention comprise a reversible modification such that the polymerase has substantially reduced activity until the polymerase is heated to temperatures sufficient to denature DNA, e.g., at least 60° C. and generally about 80-95° C. Such modifications are useful for, e.g., preventing non-specific extension or degradation of nucleic acid substrates at ambient temperatures.

In some embodiments, the activities of the enzymes are reversibly blocked by a reaction between the enzymes and an inhibiting reagent, which results in the loss of all, or nearly all (e.g., at least 80%, e.g., at least 90%), of the enzyme's activities. The inhibiting reagent is chosen such that the inhibition is reversible at elevated temperatures. In some embodiments, the inhibiting agent is an antibody that is able to inhibit one of said thermostable enzymes. Optionally instead of using an antibody, the enzyme can be inhibited by another inhibiting agent which results in a reversible chemical modification of the polymerase. As described in the present invention, reversible inactivation of thermostable enzymes can be carried out by chemical modification of lysine residues. For example, chemical modification of lysine can be performed by acid anhydrides (see. e.g. EP 0 962 526, U.S. Pat. No. 5,773,258). However, chemical modification of other amino acid residues may result in a modified protein with suitable characteristics. A number of compounds have been described in the literature which react with amino groups in a reversible manner. For example, amino groups have been reversibly modified by trifluoroacetylation (see Goldberger and Anfinsen, 1962, *Biochemistry* 1:410), amidination (see Hunter and Ludwig, 1962, *J. Amer. Chem. Soc.* 84:3491), malaylation (see Butler et al., 1967, *Biochem. J.* 103:78) acetoacetylation (see Marzotto et al., 1967, *Biochem. Biophys. Res. Commun.* 26:517; and Marzotto et al., 1968, *Biochim. Biophys. Acta* 154:450), tetrafluorosuccinylation (see Brannitzer et al., 1968, *Hoppe-Seylers's Z. Physiol. Chem.* 349:265), and citraconylation

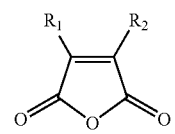

(see Dixon and Perham, 1968, *Biochem. J.* 109:312-314; and Habeeb and Atassi, 1970, *Biochemistry* 9 (25):4939-4944.

Exemplary reagents for the chemical modification of the epsilon-amino group of lysine residues are dicarboxylic acid anhydrides. See, U.S. Pat. No. 5,773,258; US Patent Publication No. 2004/0115639. Therefore, in some embodiments, the reversibly modified polymerase is produced by a reaction of a mixture of the enzyme and a modifier reagent, wherein said reaction is carried out at alkaline pH at a temperature which is less than about 25°, wherein said reagent is dicarboxylic anhydride of the general formula:

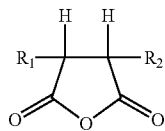

where $R_1$ and $R_2$ are hydrogen or organic radicals, which may be linked, or of the general formula:
where $R_1$ and $R_2$ are organic radicals, which may be linked, and the hydrogen are cis and wherein said reaction results in essentially complete inactivation of enzyme activity.

The organic radical may be directly attached to the ring by a carbon-carbon bond or through a carbon-hereoatom bond, such as a carbon-oxygen, carbon-nitrogen, or carbon-sulphur bond. The organic radicals may also be linked to each other to form a ring structure as in, for example, 3,4,5,6-tetrahydrophthalic anhydride.

Examples of the exemplary reagents include maleic anhydride; substituted maleic anhydrides such as citraconic anhydride, cis-aconitic anhydride, and 2,3-dimethylmaleic anhydride; exo-cis-3,6-endoxo-$\Delta.^4$-tetrahydropthalic anhydride; and 3,4,5,6-tetrahydrophthalic anhydride. The reagents are commercially available from, for example, Aldrich Chemical Co. (Milwaukee, Wis.), Sigma Chemical Co. (St. Louis, Mo.), or Spectrum Chemical Mfg. Corp (Gardena, Calif.).

V. Template Nucleic Acids

Target nucleic acids can come from a biological or synthetic source. The target can be, for example, DNA or RNA. Generally, where amplicons are generated, the amplicons will be composed of DNA, though ribonucleotides or synthetic nucleotides can also be incorporated into the amplicon. Where one wishes to detect an RNA, the amplification process will typically involve the use of reverse transcription, including for example, reverse transcription PCR (RT-PCR).

Specific target sequences can include, e.g., viral nucleic acids (e.g., human immunodeficiency virus (HIV), hepatitis virus B (HBV), (cytomegalovirus (CMV), parvo B19 virus, Epstein-Barr virus, hepatitis virus C(HCV), human papilloma virus (HPV), Japanese encephalitis virus (JEV), West Nile virus (WNV), St. Louis encephalitis virus (SLEV), Murray Valley encephalitis virus, and Kunjin virus), bacterial nucleic acids (e.g., *S. aureus, Neisseria meningitidis, Plasmodium falciparum, Chlamydia muridarum, Chlamydia trachomatis*), mycobacteria, fungal nucleic acids, or nucleic acids from animals or plants. In some embodiments, the target nucleic acids are animal (e.g., human) nucleic acids or are derived from an animal (e.g., human) sample (i.e., viral or other pathogenic organism nucleic acids may be present in a sample from an animal biopsy, blood sample, urine sample, fecal sample, saliva, etc.). In some embodiments, the target nucleic acids are, for example, human genetic regions that may include variants associated with disease (e.g., cancer, diabetes, etc.).

VI. Primer Extension Reactions

The primer extension reaction conditions are generally designed such that the oligonucleotide as a whole will hybridize to a target sequence even if there are some mismatches between the oligonucleotide and the target. Those of skill in the art will appreciate that the melting temperature of primers and probes can be determined and the amplification temperature can be controlled to allow for a sufficiently low temperature for oligonucleotide annealing and yet a sufficiently high temperature to achieve the desired amount of primer specificity.

Conditions suitable for primer extension are known in the art. See, e.g., Sambrook et al., supra. See also Ausubel et al., *Short Protocols in Molecular Biology* (4th ed., John Wiley & Sons 1999). Generally, a primer is annealed, i.e., hybridized, to a target nucleic acid to form a primer-template complex. The primer-template complex is contacted with the DNA polymerase and free nucleotides in a suitable environment to permit the addition of one or more nucleotides to the 3' end of the primer, thereby producing an extended primer complementary to the target nucleic acid. As discussed herein, prior to extension of the primer, one or more nucleotides of the 3' portion of the oligonucleotide can be excised by the proofreading activity of the polymerase. The primer can include, e.g., one or more nucleotide analog(s). In addition, the free nucleotides can be conventional nucleotides, unconventional nucleotides (e.g., ribonucleotides or labeled nucleotides), or a mixture thereof. In some variations, the primer extension reaction comprises amplification of a target nucleic acid. Conditions suitable for nucleic acid amplification using a DNA polymerase and a primer pair are also known in the art (e.g., PCR amplification methods). See, e.g., Sambrook et al., supra; Ausubel et al., supra; *PCR Applications: Protocols for Functional Genomics* (Innis et al. eds., Academic Press 1999. In other, non-mutually exclusive embodiments, the primer extension reaction comprises reverse transcription of an RNA template (e.g., RT-PCR). Use of the present mutant polymerases, which for example provide an improved extension rate or otherwise improve the reaction, e.g., allow for the ability to perform such primer extension reactions with relatively short incubation times, decreased enzyme concentrations, and/or increased product yield.

In some embodiments, primers that flank, but do not hybridize directly to a target SNP position are used in primer extension reactions in which the primers hybridize to a region adjacent to the target SNP position (i.e., within 1, 2, 3, or more nucleotides from the target SNP site). During the primer extension reaction, a primer is typically not able to extend past a target SNP site if a particular nucleotide (allele) is present at that target SNP site, and the primer extension product can be detected in order to determine which SNP allele is present at the target SNP site. For example, particular ddNTPs can used in the primer extension reaction to terminate primer extension once a ddNTP is incorporated into the extension product (e.g., a primer extension product which includes a ddNTP at the 3'-most end of the primer extension product, and in which the ddNTP is a nucleotide of a SNP to be detected).

In certain embodiments, PCR reactions are carried out as an automated process, which utilizes a thermostable enzyme. In this process the reaction mixture is cycled through a denaturing step, a primer (and optionally, probe) annealing step, and a synthesis step in which cleavage and displacement occur simultaneously with primer dependent template extension. In some embodiments, the methods described herein are performed using a system. Optionally, for example, thermal cyclers, such as those commercially available from, e.g., Applied Biosystems (Foster City, Calif., USA), which are designed for use with thermostable enzymes, may be utilized.

Hybridization of primers or probes to target nucleic acids can be accomplished by choosing appropriate hybridization conditions. The stability of the oligonucleotide:target nucleic acid hybrid is typically selected to be compatible with the assay and washing conditions so that stable, detectable hybrids form only between the primers/probes and target nucleic acids. Manipulation of one or more of the different assay parameters determines the exact sensitivity and specificity of a particular hybridization assay.

More specifically, hybridization between complementary bases of DNA, RNA, PNA, or combinations of DNA, RNA and PNA, occurs under a wide variety of conditions that vary in temperature, salt concentration, electrostatic strength, buffer composition, and the like. Examples of these conditions and methods for applying them are described in, e.g., Tijssen, *Hybridization with Nucleic Acid Probes*, Vol. 24, Elsevier Science (1993), and Hames and Higgins, supra, which are both incorporated by reference. Hybridization generally takes place between about 0° C. and about 70° C., for periods of from about one minute to about one hour, depending on the nature of the sequence to be hybridized and its length. However, it is recognized that hybridizations can occur in seconds or hours, depending on the conditions of the reaction. To illustrate, typical hybridization conditions for a mixture of two 20-mers is to bring the mixture to 68° C., followed by cooling to room temperature (22° C.) for five minutes or at very low temperatures such as 2° C. in 2 microliters. Hybridization between nucleic acids may be facilitated using buffers such as Tris-EDTA (TE), Tris-HCl and HEPES, salt solutions (e.g. NaCl, KCl, $CaCl_2$), or other aqueous solutions, reagents and chemicals. Examples of these reagents include single-stranded binding proteins such as Rec A protein, T4 gene 32 protein, *E. coli* single-stranded binding protein and major or minor nucleic acid groove binding proteins. Other examples of such reagents and chemicals include divalent ions, polyvalent ions and intercalating substances such as ethidium bromide, actinomycin D, psoralen, and angelicin.

In some embodiments, the primer extension reaction (e.g., including PCR) is monitored in "real-time" and is optionally quantitative. See, e.g., *Real-Time PCR: An Essential Guide*, Horizon Scientific Press (2004), Innis et al. (Eds.). Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol Biotechnol.* 20(2):163-79 (2002).

To quantify the amount of specific RNA in a sample, a standard curve may be generated from run-off transcription of a plasmid containing the gene of interest. Standard curves may be generated using the threshold values (Ct) values determined in the real-time PCR, which are related to the initial cDNA concentration used in the assay. In addition, a standard curve may be generated for a standard polynucleotide (e.g., a previously quantified sequence). This permits standardization of initial RNA content of a biological sample to the amount of standard for comparison purposes. See, e.g., THE PCR TECHNIQUE: QUANTITATIVE PCR (J. Larrick, ed., 1997).

Any method for detection of primer extension (including amplification) products can be used. In some embodiments, a labeled nucleic acid probe that specifically binds (i.e., hybridizes) to the reaction product is used to detect accumulation of the product. One method for detection of amplification products is the 5' nuclease PCR assay (using e.g., COBAS TaqMan 48 Analyzer™ (Roche Molecular Systems, Pleasanton, Calif.)). See, e.g., Holland et al., *Proc. Natl. Acad. Sci. USA* 88: 7276-7280 (1991); Lee et al., *Nucleic Acids Res.* 21: 3761-3766 (1993); U.S. Pat. Nos. 6,214,979; 5,804,375; 5,487,972; and 5,210,015. This assay detects the accumulation of a specific PCR product by hybridization and cleavage of a doubly labeled fluorogenic probe during the amplification reaction. The fluorogenic probe may consist of an oligonucleotide (e.g., that hybridizes to a desired target nucleic acid or its complement) labeled with both a fluorescent reporter dye and a quencher dye. During PCR, this probe is cleaved by the 5'-nuclease activity of DNA polymerase if, and only if, it hybridizes to the segment being amplified. Cleavage of the probe generates an increase in the fluorescence intensity of the reporter dye.

Another method of detecting amplification products that relies on the use of energy transfer is the "molecular beacon probe" method described by Tyagi and Kramer (*Nature Biotech.* 14:303-309 (1996)), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in "open conformation," and fluorescence is detected, while those that remain unhybridized will not fluoresce (Tyagi and Kramer, *Nature Biotechnol.* 14: 303-306 (1996). As a result, the amount of fluorescence will increase as the amount of PCR product increases, and thus may be used as a measure of the progress of the PCR.

Other types of probes useful for real time PCR methods include Scorpion™ probes, which are available in "uni-labeled" and "bi-labeled" formats from Proligo, C (Boulder, Colo.). See, also, Bates et al., *Mol. Plant Pathol.* 2(5):275-280 (2001). Those of skill in the art will recognize that other methods of quantitative amplification are also available.

VII. Reaction Mixtures

The present invention also provides reaction mixtures of the reagents as described herein. Reaction mixtures can comprise, for example, an oligonucleotide that comprises a modified nucleotide that is not removed by polymerase 3'-5' exonuclease activity and that is not at the 3' or 5' end of the oligonucleotide. Specific embodiments of the oligonucleotides described herein are specifically contemplated to be optionally included in the reaction mixtures of the invention. In some embodiments, the reaction mixture further comprises a polymerase having 3'-5' exonuclease activity.

Optionally, the reaction mixture also comprises a biological sample (e.g., nucleic acids from an organism). In some embodiments, the reaction mixtures comprise a template nucleic acid. In some embodiments, the 3' portion of the oligonucleotide is 70-100% complementary to the template nucleic acid or is otherwise complementary to the template as described herein.

VIII. Kits

The present invention also provides for kits comprising one or more reagents as described herein. In some embodiments, the kits comprise, for example, an oligonucleotide that comprises a modified nucleotide that is not removed by polymerase 3'-5' exonuclease activity and that is not at the 3' or 5' end of the oligonucleotide. Specific embodiments of the oligonucleotides described herein are specifically contemplated to be optionally included in the kits of the invention. In some embodiments, the reaction mixture further comprises a polymerase having 3'-5' exonuclease activity. The kits of the invention can optionally include instructions for use. Such instructions can be in paper, electronic (e.g., on a CD-ROM or DVD), or other form.

IX. Systems

In some embodiments, the invention provides integrated systems for performing and/or detecting the results of the primer extension reactions of the present invention. The systems can include instrumentation and means for interpreting and analyzing collected data, especially where the means for deriving the results of the primer extension reactions comprise algorithms and/or electronically stored information (e.g., collected fluorescence data, predetermined options for extension products, etc). Each part of an integrated system can be functionally interconnected, and in some cases, physically connected. In some embodiments, the integrated system is automated, where there is no requirement for any manipulation of the sample or instrumentation by an operator following initiation of the analysis.

A system of the invention can include instrumentation. For example, the invention can include a detector such as a fluorescence detector (e.g., a fluorescence spectrophotometer). A detector or detectors can be used in conjunction with the invention, e.g., to monitor/measure primer extension reactions, e.g., as measured as a change in fluorescence. A detector can be in the form of a multiwell plate reader to facilitate the high-throughput capacity of the assay.

In some embodiments, the integrated system includes a thermal cycling device, or thermocycler, for the purpose of controlling the temperature of the reaction. In some embodiments, the thermal cycling device and the detector are an integrated instrument, where the thermal cycling and emission detection (e.g., fluorescence detection) are done in the same device.

A detector, e.g., a fluorescence spectrophotometer, can be connected to a computer for controlling the spectrophotometer operational parameters (e.g., wavelength of the excitation and/or wavelength of the detected emission) and/or for storage of data collected from the detector (e.g., fluorescence measurements during amplification cycles). The computer may also be operably connected to the thermal cycling device to control the temperature, timing, and/or rate of temperature change in the system. The integrated computer can also contain the "correlation module" where the data collected from the detector is analyzed (electronically). In some embodiments, the correlation module comprises a computer program for analysis of the generated data, e.g., determining the presence or absence of a viral or other pathogen, or presence or absence of a SNP or other potential target to be detected, e.g., by comparing the data generated with a database of possible outputs.

In some embodiments, detectors are structured to detect detectable signals produced, e.g., in or proximal to another component of the given assay system (e.g., in container, on a solid support, etc.). Suitable signal detectors that are optionally utilized, or adapted for use, herein detect, e.g., fluorescence, phosphorescence, radioactivity, absorbance, refractive index, luminescence, mass, or the like. Detectors optionally monitor one or a plurality of signals from upstream and/or downstream of the performance of, e.g., a given assay step. For example, detectors optionally monitor a plurality of optical signals, which correspond in position to "real-time" results. Example detectors or sensors include photomultiplier tubes, CCD arrays, optical sensors, temperature sensors, pressure sensors, pH sensors, conductivity sensors, scanning detectors, or the like. More specific exemplary detectors that are optionally utilized in performing the methods of the invention include, e.g., resonance light scattering detectors, emission spectroscopes, fluorescence spectroscopes, phosphorescence spectroscopes, luminescence spectroscopes, spectrophotometers, photometers, and the like. Detectors are also described in, e.g., Skoog et al., *Principles of Instrumental Analysis*, 5th Ed., Harcourt Brace College Publishers (1998) and Currell, *Analytical Instrumentation: Performance Characteristics and Quality*, John Wiley & Sons, Inc. (2000), both of which are incorporated by reference.

The systems of the invention also typically include controllers that are operably connected to one or more components (e.g., detectors, thermal modulators, fluid transfer components, etc.) of the system to control operation of the components. More specifically, controllers are generally included either as separate or integral system components that are utilized, e.g., to receive data from detectors, to effect and/or regulate temperature in the containers, to effect and/or regulate fluid flow to or from selected containers, or the like. Controllers and/or other system components is/are optionally coupled to an appropriately programmed processor, computer, digital device, or other information appliance (e.g., including an analog to digital or digital to analog converter as needed), which functions to instruct the operation of these instruments in accordance with preprogrammed or user input instructions, receive data and information from these instruments, and interpret, manipulate and report this information to the user. Suitable controllers are generally known in the art and are available from various commercial sources.

Any controller or computer optionally includes a monitor, which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. These components are illustrated further below.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming, e.g., such as controlling fluid flow regulators in response to fluid weight data received from weight scales or the like.

EXAMPLE

The DNA polymerases generally used for PCR and RT/PCR tend to have difficulty amplifying targets with mismatches near the 3'-end of the primers. Unfortunately, this is commonly observed for targets that have significant sequence heterogeneity such as the targets in HIV and HCV diagnostic assays. The reduced ability of the DNA polymerase to misextend mismatches at the 3'-end is even more pronounced when the primers are modified by alkylation. Alkylation of primers reduces primer/dimer effects (see, e.g., U.S. Pat. Nos. 6,001,611; 6,794,142), however, the methods of the invention can be performed without alkylated primers. One methodology to minimize the impact of these terminal mismatches is to remove the mismatches entirely prior to extending the oligonucleotide primer. We have evaluated the use of DNA polymerases with modulated 3'-5' exonuclease (proofreading) activity to alleviate mismatch intolerance and compared them to enzymes devoid of proofreading activity. Proofreading activity of the DNA polymerases can be blocked by the use of 2'-amino-modified bases in the primer sequence. We engineered primers with these blocking groups to provide the desired extent of proofreading degradation. Primers were designed with the 2-'amino modification either at the penultimate base (to block all proofreading) or upstream of potential mismatches at the 3'-end (to allow proofreading of the 3'-end, but not allow the enzyme to degrade the oligonucleotide further). The results of these studies demonstrate that proofreading activity allows DNA polymerases to efficiently amplify these mismatched targets. Thus, we have demonstrated an approach to improve performance of amplification systems challenged by sequence heterogeneity under oligonucleotide primers.

The chimeric DNA Polymerase, CS5, was created by combining the 5'-3' exonuclease domain from *Thermus* sp. Z05 and the 3'-5' exonuclease and DNA polymerase domains from *Thermatoga maritima*. See, Schonbrunner et al., *Biochemistry* 45:12786-12795 (2006). This DNA Polymerase was used to create a collection of chimeric mutant DNA polymerases with attenuated proofreading activity, with CS5L (CS5 with mutation L329A) retaining approximately 10% proofreading activity and CS6 being devoid of proofreading. See, Schonbrunner et al., *Biochemistry* 45:12786-12795 (2006). In a second round of mutagenesis, enzymes with improved extension rates on a primed M13 DNA template in the presence of SYBR Green were selected. Some of these CS5L mutants displayed the ability to perform long sensitive RT/PCR. The most promising mutation was D640G. We transferred these mutations from the CS5 DNA polymerase backbone to the 3'-5' exonuclease and DNA polymerase domains of the wild type Tma DNA polymerase. The Tma6D and TmaLD DNA polymerases contain the D640G "faster-extender" mutation but Tma6D is devoid of proofreading activity and TmaLD has reduced proofreading activity. Similarly, we transferred the homologous D640G DNA polymerase domain mutation from CS5 into Z05 (D580G).

The proofreading activity of the DNA polymerase is limited by the use of 2'-amino modified bases within the primer sequence. Primers were designed with the 2'-amino modification either at the penultimate base (to completely block proofreading) or at the N-6 position of the primer which is upstream of the potential mismatches at the 3'-end (to allow for limited proofreading). These primers were compared to alkylated primers with no 2'-amino modifications. The use of enzymes with modulated proofreading activity and the use of new DNA polymerases to alleviate the performance reduction caused by mismatches at the 3' termini of the primers has been evaluated.

Enzymatic Activity

FIG. 1 provides a schematic illustration of mismatch editing. The two Ts in the primer sequence are mismatched to the target. The DNA polymerase removes the mismatches on the primer prior to extending it. The primer is protected from further enzymatic degradation by the 2'-amino modification in the primer sequence. This process generates a primer that is perfectly matched to its target.

RT/PCR of Matched and Mismatched Targets

Figure 2B:
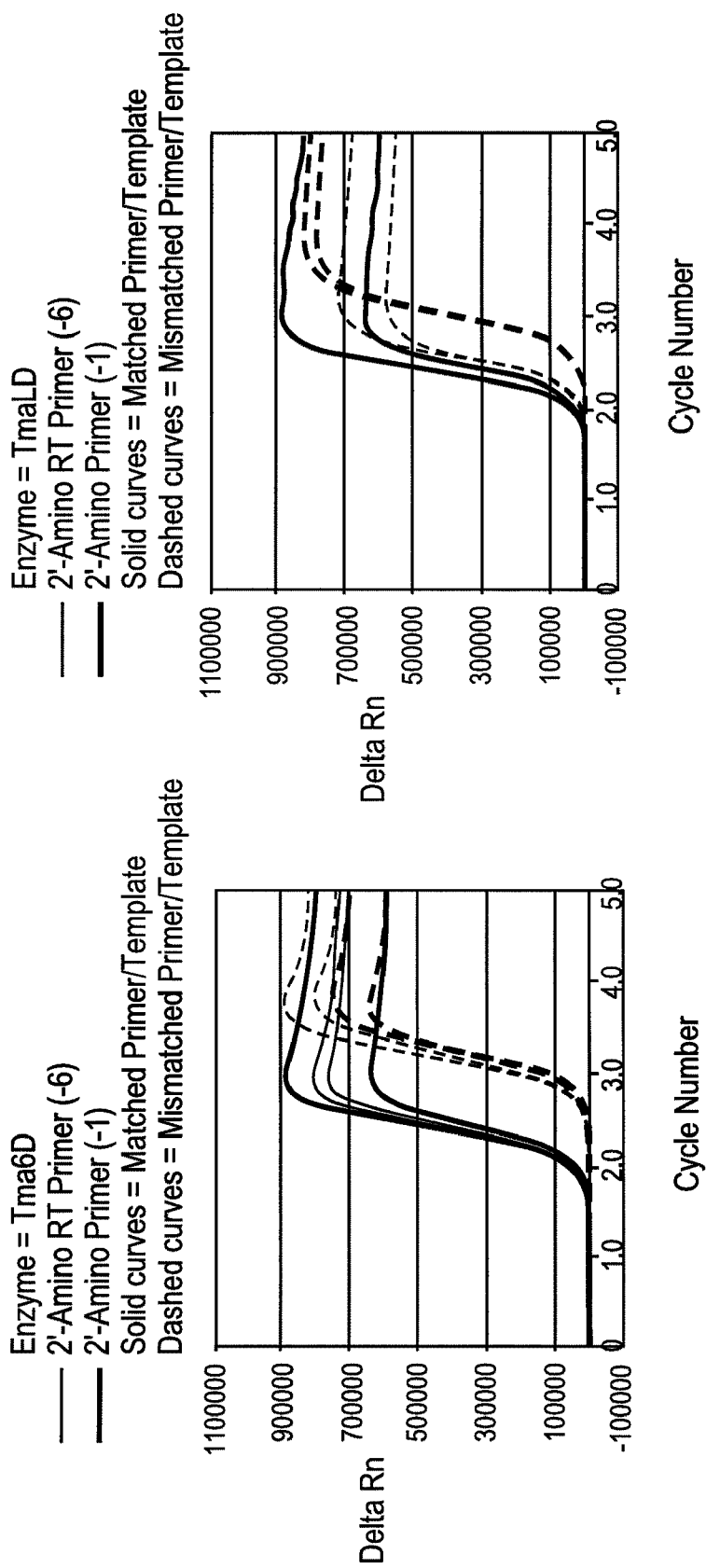
FIG. 2B illustrates accumulation of product as a function of cycle number for matched and mismatched primers in PCR reactions including a polymerase substantially lacking 3'-5' exonuclease activity (left panel) or having 3'-5'exonuclease activity (right panel).

FIG. 2A shows primers and templates used for amplification of the GAG region of HIV. FIG. 2B shows the results of HIV RT/PCR (SYBR Green) with a 15 minute RT step using either a perfectly matched (in the 3' portion) transcript or a mismatched transcript (T97599-1). The 2'-amino-modifications on the RT primer were at the penultimate position (−1) or at the N-6 position from the primer 3'-terminus.

Figure 2C:
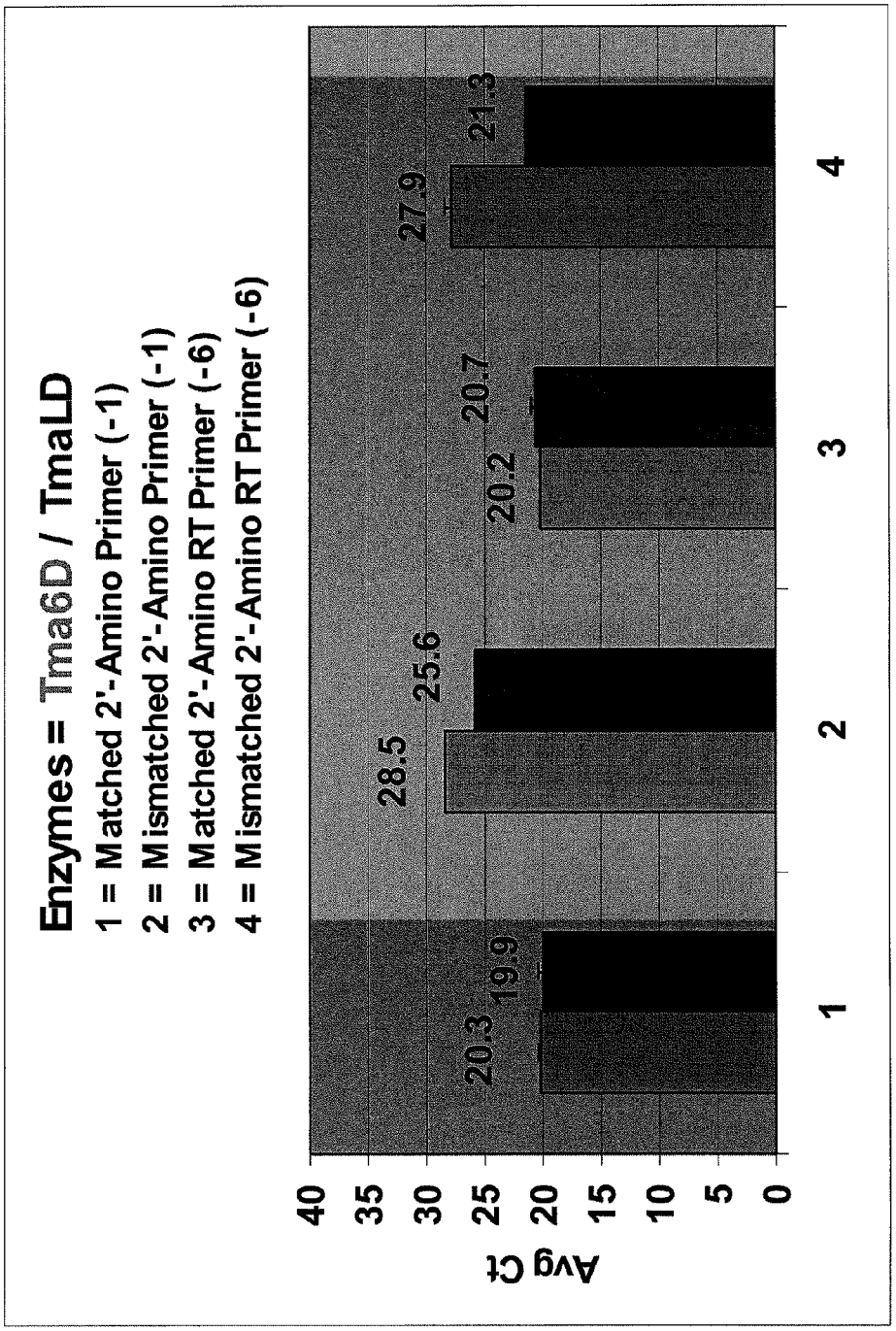
FIG. 2C illustrates the average difference in Ct for reactions including a polymerase substantially lacking 3'-5' exonuclease activity or having 3'-5'exonuclease activity.

The Tma6D DNA polymerase (no proofreading activity) has an ~8 Ct delay for the mismatched target with the 2'-amino-modified primers (−1 and −6). The proofreading DNA polymerase TmaLD has an ~6 cycle delay for the mismatched target with the −1 2'-amino-modified primer but less than 1 cycle delay with the −6 amino-modified primer (the 2'-amino group upstream of the mismatches). Ct differences are also illustrated in FIG. 2C.

Amplification with Alkyl-Modified Primers

Figure 3:
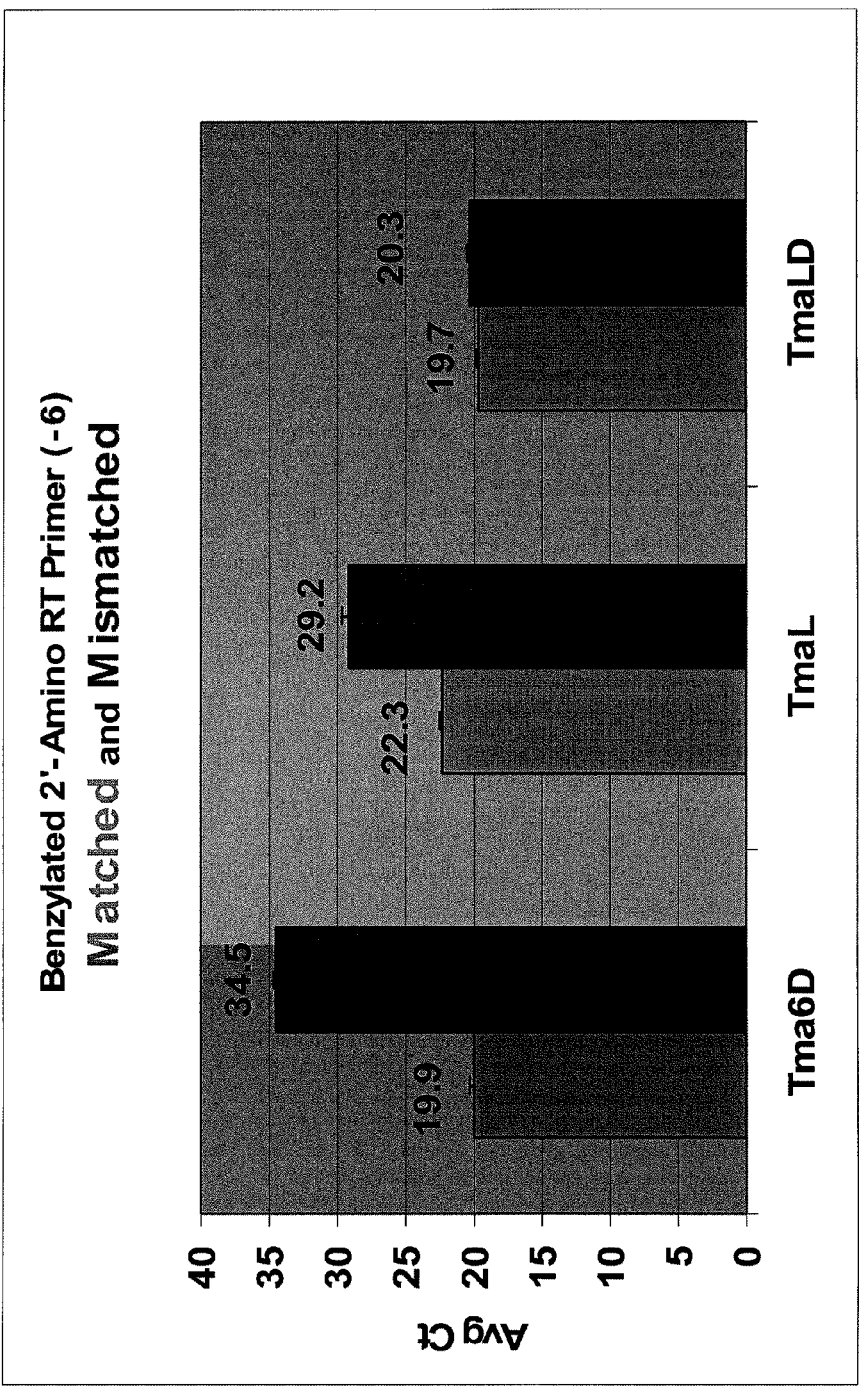
FIG. 3 illustrates average Ct values of matched and mismatched primers involving different enzymes and with or without benzylated primers.

The difficulty of extending mismatches at the 3'-end is exacerbated when the primers are modified with benzyl groups (causing a larger Ct delay). See, FIG. 3. The Tma6D DNA Polymerase shows an ~15 cycle delay using the mismatched target with a benzylated primer while the proofreading DNA polymerase TmaLD shows <1 cycle delay. The TmaL DNA Polymerase (also a proofreading enzyme) shows an ~7 cycle delay for the mismatched target. These results suggest that the proofreading activity was responsible for improving the amplification of the mismatched target and that the D640G mutation in Tma improved it further. These results confirm that alkylated primers are degraded by the 3'-5' exonuclease (proofreading) activity of a DNA polymerase.

Proofreading Enzyme Added to HIV-1 MMX

Figure 4A:
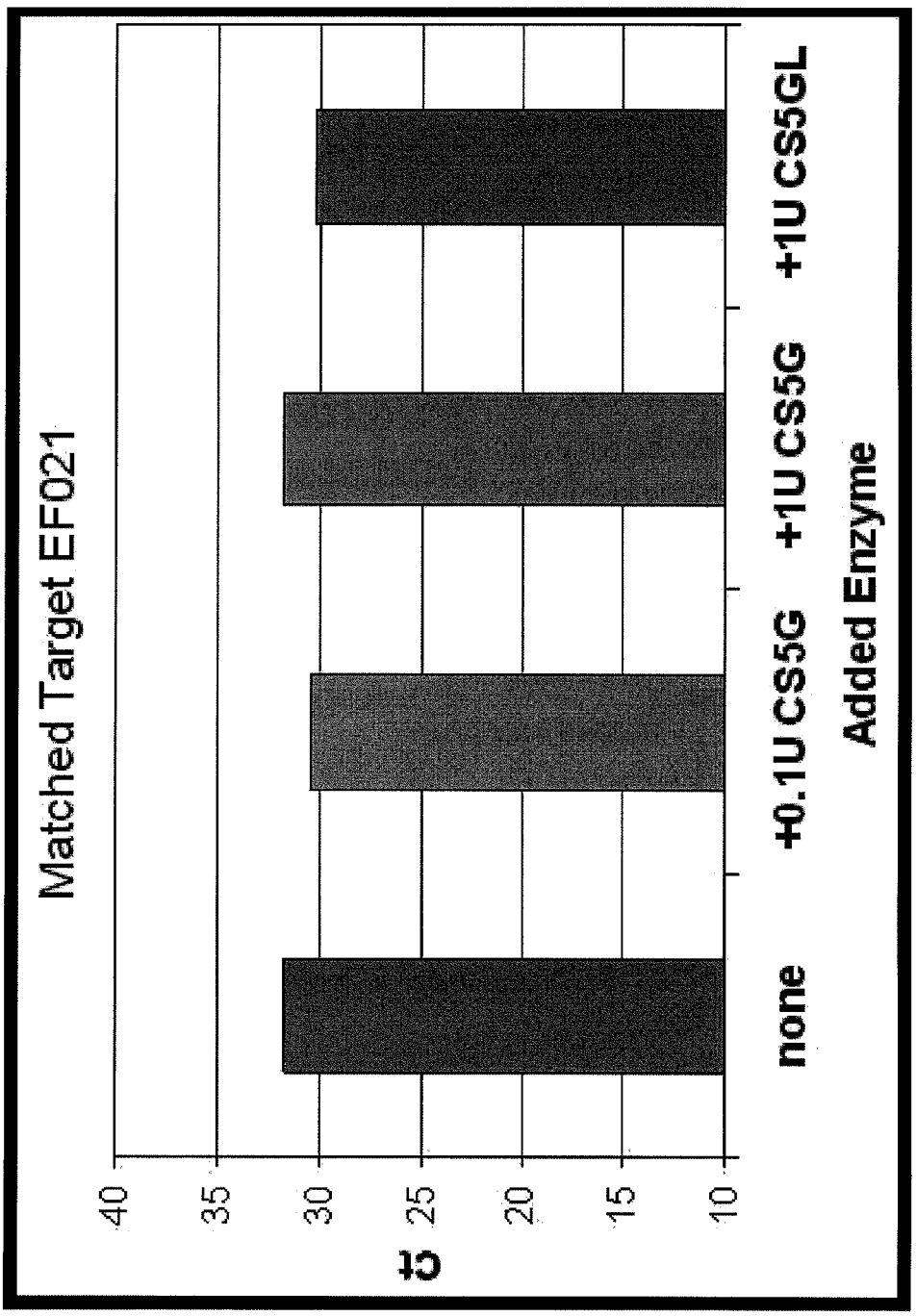
FIGS. 4A-B illustrates the average Ct value for matched (A) and mismatched (B) primers for the HIV target sequence using only a polymerase substantially lacking 3'-5' exonuclease activity ("none") or further including an amount of a polymerase having 3'-5' exonuclease activity.
Figure 4B:
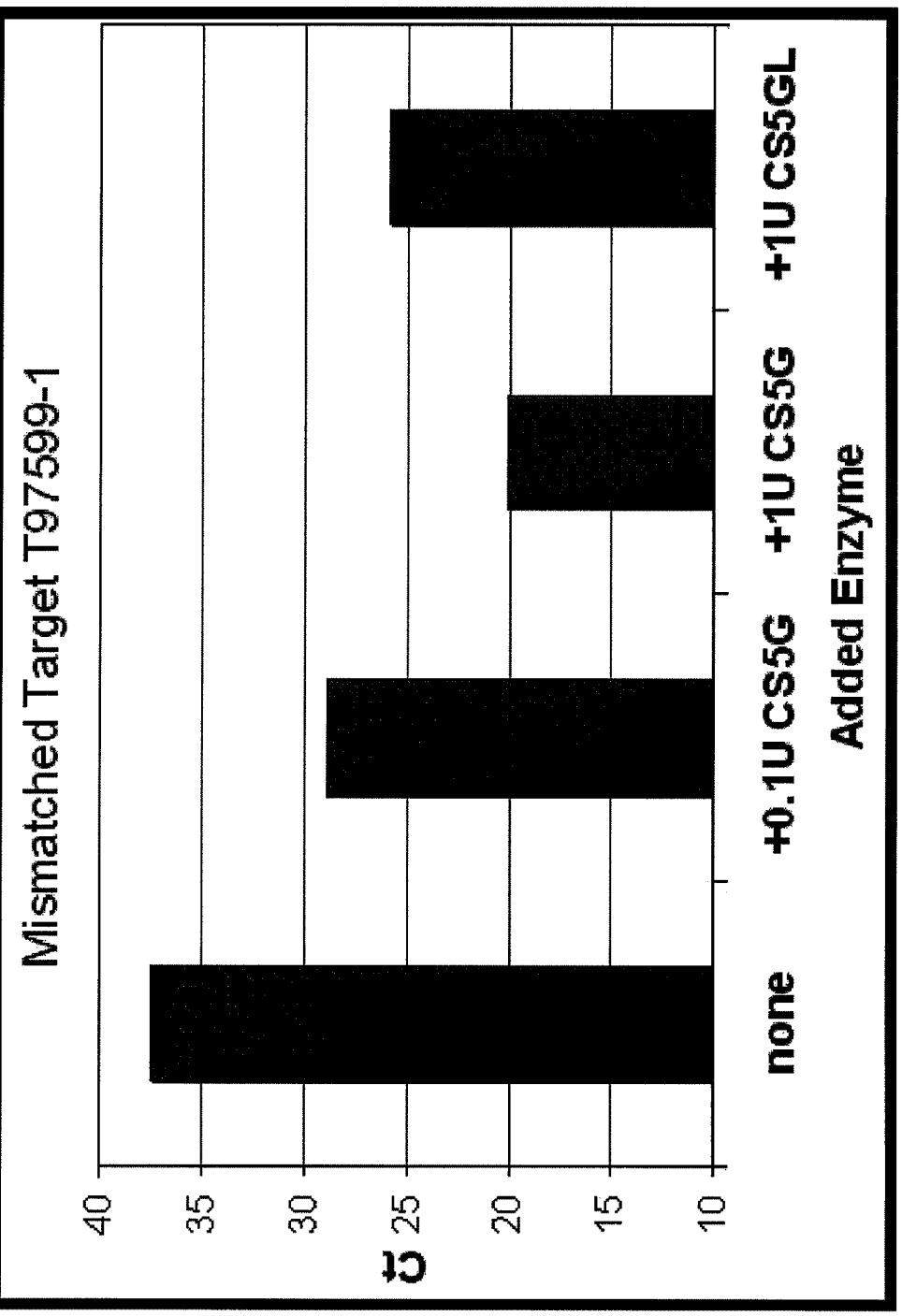

Proofreading enzymes CS5G or CS5GL were spiked into the manufactured Mastermix of the COBAS AmpliPrep/COBAS TaqMan HIV-1 test. Favorable results were achieved when either 0.1 U of CS5G or 1 U of CS5GL DNA polymerases was added. See, FIGS. 4A and 4B. Using the mismatched target T97599-1, the addition of either 0.1 U of CS5G or 1 U of CS5GL DNA polymerase showed an 8.5 to 11.6 cycle earlier Ct than Z05 DNA polymerase alone. The quantitation standard (QS) showed a 2.1 to 3.9 cycle earlier Ct, respectively. Thus the addition of a proofreading enzyme leads to more accurate copy number determination for this mismatched transcript. With the matched target, EF021, the results indicated that the addition caused little change in quantification.

conclusions

We have demonstrated multiple approaches to improve performance of amplification systems challenged by mismatched templates. The proofreading activity of a DNA polymerase (e.g. TmaLD) was shown to successfully amplify targets with mismatches at the 3'-end of the primers. When primers with 2'-amino modified nucleotides that restricted the extent of proofreading were used, i.e. in the penultimate position of the primer sequence, the amplification behaved as if a non-proofreading DNA polymerase was used (comparable to Tma6D). However, when the 2'-amino-modification was located upstream of the mismatches, degradation past the mismatches to one base short of the 2'-amino group allowed for a primer perfectly matched to its target and thereby improved amplification.

Alkyl modifications exacerbate the difficulty in extending 3'-mismatches (causing a larger Ct delay). These results suggest that the proofreading activity was responsible for improving the amplification of the mismatched target and that the D640G mutation in Tma (D580G in Z05) improved it further. These results confirm that benzylated primers are degraded by the 3'-5' exonuclease (proofreading) activity of a DNA polymerase.

The addition of a proofreading enzyme to current Z05-based viral TaqMan tests may be a solution to improving performance in existing amplification systems challenged by sequence heterogeneity under oligonucleotide primers.

Specific mutations characterized in the Tma and Z05 DNA polymerases may confer a double benefit in systems using alkylated primers when a mismatched template occurs. The D640G mutation in Tma DNA polymerase and mutations at the D580 position in Z05 DNA polymerase (such as Z05D) improve extension of 3' modified primers and improve mismatch tolerance.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of performing a primer extension reaction, the method comprising,
   a. contacting an oligonucleotide to (i) a template nucleic acid and (ii) a thermostable nucleic acid polymerase having 3'-5' exonuclease activity, wherein:
      i. the oligonucleotide comprises a modified nucleotide that is not removed by the 3'-5' exonuclease activity, wherein the modified nucleotide comprises a 2' moiety selected from the group consisting of: amino, OH, O-phosphate, and phosphorothioate;
      ii the modified nucleotide is not at the 3' or 5' terminal nucleotide nor at the 3' penultimate nucleotide of the oligonucleotide;
      iii. the oligonucleotide has a 3' portion and a 5' portion, wherein the 3' portion comprises the nucleotides in the oligonucleotide that are 3' of the modified nucleotide and the 5' portion comprises the nucleotides in the oligonucleotide that are 5' of the modified nucleotide; and
      iv. the contacting step is performed under conditions suitable to allow the polymerase to edit the 3' portion of the oligonucleotide in a template-specific manner if the 3' portion of the oligonucleotide is not 100% complementary to the template nucleic acid; and
   b. performing a primer extension reaction by extending the oligonucleotide in a template-dependent manner.

2. The method of claim 1, wherein the template nucleic acid is from a viral or bacterial genome.

3. The method of claim 1, wherein the modified nucleotide is between 2-10 nucleotides from the 3' end of the oligonucleotide.

4. The method of claim 1, wherein step b comprises a polymerase chain reaction.

5. The method of claim 1, wherein the modified nucleotide does not comprise a fluorescent moiety.

6. A method of detecting the presence, absence or amount of a biological entity in a biological sample, the method comprising,
   a. contacting an oligonucleotide to (i) a biological sample suspected of having a nucleic acid from the biological entity and (ii) a thermostable nucleic acid polymerase having 3'-5' exonuclease activity, wherein the oligonucleotide is substantially complementary to the nucleic acid from the biological entity, wherein;
      i. the oligonucleotide comprises a modified nucleotide that is not removed by the 3'-5' exonuclease activity, wherein the modified nucleotide comprises a 2' moiety selected from the group consisting of: amino, OH, O-phosphate, and phosphorothioate;

ii the modified nucleotide is not at the 3' or 5' terminal nucleotide nor at the 3' penultimate nucleotide of the oligonucleotide;
iii. the oligonucleotide has a 3' portion and a 5' portion, wherein the 3' portion comprises the nucleotides in the oligonucleotide that are 3' of the modified nucleotide and the 5' portion comprises the nucleotides in the oligonucleotide that are 5' of the modified nucleotide; and
iv. the contacting step is performed under conditions suitable to allow the polymerase to edit the 3' portion of the oligonucleotide in a template-specific manner if the 3' portion of the oligonucleotide is not 100% complementary to the nucleic acid from the biological entity; and
b. performing a polymerase chain reaction thereby extending the oligonucleotide in a template-dependent manner to produce a polynucleotide product complementary to the nucleic acid from the biological entity;
c. quantifying the polynucleotide product, or its complement; and
d. correlating the amount of polynucleotide product, or complement thereof, to the amount or presence or absence of the biological entity in the biological sample.

7. The method of claim 6, wherein the quantifying step comprises quantitative real-time PCR.

8. The method of claim 6, wherein the PCR comprises a step under conditions that allow extension of the oligonucleotide whether or not there are zero, one, two or three mismatches between the oligonucleotide and the viral nucleic acid and wherein the oligonucleotide has one or more mismatch with the nucleic acid from the biological entity and wherein the 3'-5' exonuclease activity of the polymerase edits the oligonucleotide to result in a polynucleotide product that is fully complementary to the polynucleotide product.

9. The method of claim 6, wherein the performing step further comprises one or more thermostable nucleic acid polymerases, some of which substantially lack 3'-5' exonuclease activity.

* * * * *

SEQUENCE LISTING

```
<160> NUMBER OF SEQ ID NOS: 8

<210> SEQ ID NO 1
<211> LENGTH: 29
<212> TYPE: DNA
<213> ORGANISM: Artificial Sequence
<220> FEATURE:
<223> OTHER INFORMATION: synthetic upstream primer in HIV GAG region
<221> NAME/KEY: modified_base
<222> LOCATION: (26)...(26)
<223> OTHER INFORMATION: n = 2'-amino (ribo) c (E)

<400> SEQUENCE: 1
agtgggggga catcaagcag ccatgnaaa                                  29

<210> SEQ ID NO 2
<211> LENGTH: 30
<212> TYPE: DNA
<213> ORGANISM: Artificial Sequence
<220> FEATURE:
<223> OTHER INFORMATION: synthetic RT primer in HIV GAG region
<221> NAME/KEY: modified_base
<222> LOCATION: (29)...(29)
<223> OTHER INFORMATION: n = 2'-amino (ribo) c (E)

<400> SEQUENCE: 2
ggtactagta gttcctgcta tgtcacttnc                                 30

<210> SEQ ID NO 3
<211> LENGTH: 30
<212> TYPE: DNA
<213> ORGANISM: Artificial Sequence
<220> FEATURE:
<223> OTHER INFORMATION: synthetic RT primer in HIV GAG region
<221> NAME/KEY: modified_base
<222> LOCATION: (24)...(24)
<223> OTHER INFORMATION: n = 2'-amino (ribo) c (E)

<400> SEQUENCE: 3
ggtactagta gttcctgcta tgtnacttcc                                 30

<210> SEQ ID NO 4
<211> LENGTH: 30
<212> TYPE: DNA
<213> ORGANISM: Artificial Sequence
<220> FEATURE:
<223> OTHER INFORMATION: synthetic RT primer in HIV GAG region
<221> NAME/KEY: modified_base
<222> LOCATION: (24)...(24)
<223> OTHER INFORMATION: n = 2'-amino (ribo) c (E)
<221> NAME/KEY: modified_base
<222> LOCATION: (29)...(29)
<223> OTHER INFORMATION: n = ethyl-deoxy c (P)
<221> NAME/KEY: modified_base
<222> LOCATION: (30)...(30)
<223> OTHER INFORMATION: n = t-butyl benzyl deoxy c

<400> SEQUENCE: 4
ggtactagta gttcctgcta tgtnacttnn                                 30

<210> SEQ ID NO 5
<211> LENGTH: 29
<212> TYPE: DNA
```

```
<213> ORGANISM: Artificial Sequence
<220> FEATURE:
<223> OTHER INFORMATION: synthetic matched transcript template to
      upstream primer in HIV GAG region

<400> SEQUENCE: 5
tttgcatggc tgcttgatgt cccccccact                                              29

<210> SEQ ID NO 6
<211> LENGTH: 30
<212> TYPE: DNA
<213> ORGANISM: Artificial Sequence
<220> FEATURE:
<223> OTHER INFORMATION: synthetic matched transcript template to RT
      primer in HIV GAG region

<400> SEQUENCE: 6
ggaagtgaca tagcaggaac tactagtacc                                              30

<210> SEQ ID NO 7
<211> LENGTH: 29
<212> TYPE: DNA
<213> ORGANISM: Artificial Sequence
<220> FEATURE:
<223> OTHER INFORMATION: synthetic mismatched transcript template to
      upstream primer in HIV GAG region

<400> SEQUENCE: 7
tttgcattgc tgcttgatgg cccccaact                                               29

<210> SEQ ID NO 8
<211> LENGTH: 30
<212> TYPE: DNA
<213> ORGANISM: Artificial Sequence
<220> FEATURE:
<223> OTHER INFORMATION: synthetic mismatched transcript template to RT
      primer in HIV GAG region

<400> SEQUENCE: 8
ggccgtgaca tagcaggaac tactagtacc                                              30
```